United States Patent [19]

Desideri et al.

[11] Patent Number: 4,705,855
[45] Date of Patent: Nov. 10, 1987

[54] 1-[2-(2,4-DICHLOROPHENYL)-2-(4-SUBSTITUTED PIPERAZINE)ETHYL]-1H-IMIDAZOLES HAVING ANTIMYCOTIC AND ANTIBACTERIAL ACTIVITIES, PHARMACEUTICAL COMPOSITIONS CONTAINING THEM

[75] Inventors: Derio Desideri, San Fruttuoso di Monza; Riccardo Stradi, Milan; Alberto Milanese, San Fruttuoso di Monza, all of Italy

[73] Assignee: Rottapharm S.p.A., Varese, Italy

[21] Appl. No.: 840,495

[22] Filed: Mar. 17, 1986

[30] Foreign Application Priority Data

Apr. 15, 1985 [IT] Italy ................. 20337 A/85

[51] Int. Cl.$^4$ .................. C07D 403/06; C07D 403/14; A61K 31/495
[52] U.S. Cl. .................................................. 544/370
[58] Field of Search ......................... 544/370; 514/252

[56] References Cited

PUBLICATIONS

The Merck Index, 9th edition, 1976, 6043.
Godefroi et al., CA 72-90466v.

Primary Examiner—Donald G. Daus
Assistant Examiner—Cecilia Shen
Attorney, Agent, or Firm—Bucknam and Archer

[57] ABSTRACT

Compounds of formula I

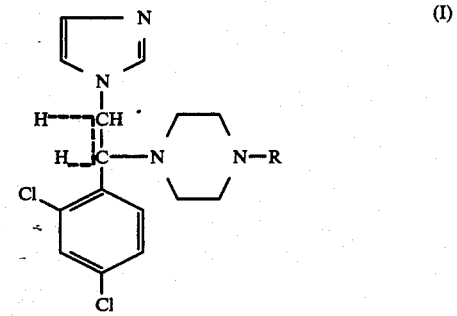

wherein R is a phenyl group; a phenyl group mono- or di-substituted by halogen atoms, methyl, methoxy, nitro, or trifluoromethyl group; or a 2-, 3- or 4-pyridyl group; and pharmaceutically acceptable acid addition salts thereof.

Compounds I are prepared by reacting N-substituted piperazines with 1-(2',4'-dichloro-benzoylmetyl)-imidazole, optionally reducing thereafter the resulting enamines.

Compounds I have antimycotic and antibacterial activities, higher than those of known comparison drugs.

3 Claims, No Drawings

1-[2-(2,4-DICHLOROPHENYL)-2-(4-SUBSTITUTED PIPERAZINE)ETHYL]-1H-IMIDAZOLES HAVING ANTIMYCOTIC AND ANTIBACTERIAL ACTIVITIES, PHARMACEUTICAL COMPOSITIONS CONTAINING THEM

The present invention relates to compounds of formula I

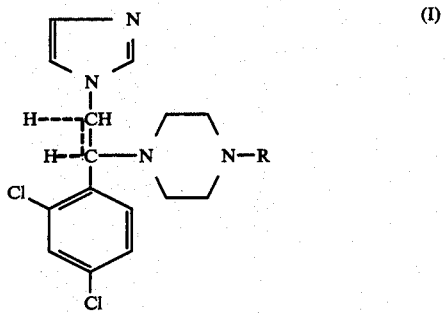

wherein R is a phenyl group; a phenyl group mono- or disubstituted by halogen atoms, methyl, methoxy, nitro, or trifluoromethyl groups; or a 2-, 3- or 4-pyridyl group; and pharmaceutically acceptable acid addition salts thereof.

The present invention relates also to a process for preparing compounds I and to pharmaceutical compositions containing them as the active ingredient.

Reduced compounds I show an asymmetric center and the invention therefore relates to the separated single enantiomers as well as mixtures thereof.

In the antimycotic field, a number of imidazole derivatives are known, having general formula II

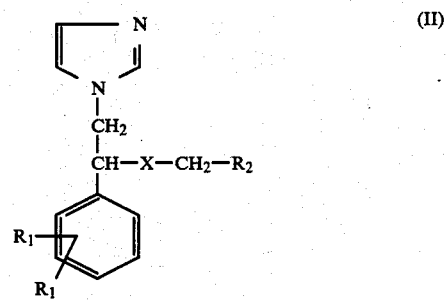

wherein at least one of the $R_1$ groups represents halogen, preferably chlorine, X is an oxygen or sulfur atom and $R_2$ is a phenyl group variously substituted by chlorine atoms or chlorinated heterocyclic groups (e.g. 2-chloro-thienyl).

Amongst compounds II, which are widely used in therapy as antimycotic for systemic or topical use, the more representative are miconazole, econazole, isoconazole, orconazole, tioconazole, sulconazole (Drugs of the future V e VII (2), 1982, 88). However, the therapeutic treatment of infections caused by mycetes asks for the availability of always new drugs, possibly endowed with a wider activity spectrum than the known drugs, active also systemically, and able to overcome the problem of the onset of resistance phenomena to the commonly used chemotherapeutics agents.

Now, it has been found that compounds of formula I have strong antimycotic and antibacterial activities against blastomycetes, hyphomycetes, Gram-positive and Gram-negative bacteria, said activities being sometimes higher than those of known drugs, particularly Miconazole.

Particularly preferred compounds are those wherein R, in formula I, is a phenyl group, substituted at the 2-, 3- or 4-positions by a fluorine or chlorine atom or by a trifluoromethyl group.

Compounds I may optionally be salified with non-toxic inorganic or organic acids, such as nitric, hydrochloric, sulphuric, fumaric, malic, maleic, succinic, cytric, acetic acids, etc.

Compounds I or the salts thereof may be administered to humans or animals in form of pharmaceutical compositions, suitably formulated with conventional excipients or carriers.

For instance, suitable formulations for the oral administration are capsules, tablets, syrups, granulates, solutions containing effective unit doses of compounds I, together with excipients such as lactose, saccharose, talc, magnesium stearate, microcrystalline cellulose, etc.

Pharmaceutical formulations for parenteral administration are injectable sterile solutions (vials or ampules), whilst for the topical administration lotions, ointments, creams, powder, etc. are envisaged.

The pharmaceutical compositions for oral or parenteral administration will contain 100 to 500 mg of compounds I, or the equivalent of the salts thereof; topical compositions will contain the active ingredient in a concentration varying from 0.1 to 10% by weight. The pharmaceutical compositions of the invention may be administered 2 to 4 times daily depending on conditions, weight and age of the patient, as well as type of infecting microorganism.

The process according to the invention consists in reacting a piperazine of formula III

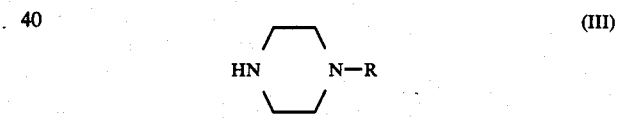

wherein R has the same meanings defined for formula I, with 1-(2,4-dichloro-benzoylmethyl)-imidazole of formula IV

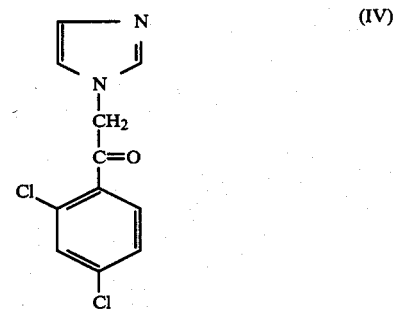

which may be prepared from 2, 2', 4'-trichloroacetophenone and imidazole.

The enamine, obtained by the reaction of III with IV, is then optionally reduced by means of one of the conventional methods for reducing enamines, e.g. by alkali hydrides such as sodium cyanoborohydride.

The reaction between III and IV is carried out in the presence of acids, preferably in anhydrous solvents, halogenated hydrocarbons, aromatic hydrocarbons, alcohols or mixtures thereof being preferred.

Aromatic hydrocarbons, such as benzene, toluene or xylene and a mixture of toluene and anhydrous butanol are particularly preferred. p-Toluenesulphonic acid is preferably used as the acid catalyst; temperature is generally the reflux temperature of the mixture. The reduction reaction with hydrides is carried out in anhydrous lower alcohols, perferably methanol.

The following non-limiting examples further illustrate the invention.

EXAMPLE 1

1-(2,4-Dichloro-benzoylmethyl)imidazole

20 Grams (0.268 mole) of imidazole were added to a solution of 30 g (0.134 mole) of 2,2', 4'-trichloroacetophenone in 225 ml of isopropanol.

The mixture was heated to reflux for 20 hours; the progress of the reaction was checked by T.L.C. (ethyl acetate 100). At the end of the reaction, isopropanol was evaporated under reduced pressure. The obtained residue was added with
   water (140 ml) at 40° C.
   $NaHCO_3$ (14 g)
under stirring.

The mixture was filtered by suction, the solid residue was taken up in 300 ml of ethyl acetate; filtered by suction again, the filtrate was dried over anhydrous $Na_2SO_4$, and the solvent was evaporated off under reduced pressure. The compound, 1-(2,4-dichloro-benzoylmethyl)-imidazole, hardly crystallizable, was dissolved in ethyl acetate and treated with 65% $HNO_3$: a precipitate formed, corresponding to the compound salified at the imidazole. The nitrate was pump filtered, washed with ethyl acetate, crystallized from ethanol to obtain a white solid, which was suspended in water and treated with an equimolecular amount of aqueous NaOH: the basic ketone was obtained, which was filtered by suction, dissolved in chloroform, and washed with water. The organic phase was dried over $Na_2SO_4$ and evaporated under reduced pressure. The obtained 1-(2,4-dichloro-benzoylmethyl)-imidazole was washed with an ethyl ether/ethyl acetate mixture.

Yield: 30%.
M.p. 170° C.
NMR and IR in agreement.

EXAMPLE 2

1-[2-(2,4-dichlorophenyl)-2-(4-phenyl-piperazine)-vinyl]-1H-imidazole

A mixture consisting of 4 g (0.0157 moles) of 1-(2,4-dichlorobenzoylmethyl)-imidazole, 5 ml (0.0314 moles, d=1,062, p=95%) of N-phenyl-piperazine in 120 ml of anhydrous toluene, containing p-toluenesulphonic as catalyst, was heated to reflux for 72 hours. The reaction was checked by NMR. Toluene was evaporated under reduced pressure, the crude product was taken up in chloroform and quickly washed with ice-water. The organic hase was dried on anhydrous $Na_2SO_4$, and chloroform was evaporated off under reduced pressure. The obtained compound was in form of an oil.

The yield of the crude compound was about 90%.
NMR in agreement.

EXAMPLE 3

1-[2-(2,4-Dichlorophenyl)-2-(4-phenyl-piperazine)ethyl]-1H-imidazole

A solution of 6.26 g (0.00157 moles of 1-[2-(2,4-dichlorophenyl)-2-(4-phenyl-piperazine)vinyl]-1H-imidazole in 20 ml of anhydrous methanol was acidified to pH 3–4 with HCl-saturated methanol. 0.7 Grams (0.0109 moles) of sodium cyanoborohydride was added to the solution. The reaction was continued for 2–3 hours, under stirring, checking by NMR. At the end of the reaction, methanol was evaporated under reduced pressure, the residue was alkalinized with aqueous 2N NaOH, added with ethyl acetate and stirred for 10 minutes. The two phases were separated, the aqueous one was extracted with ethyl acetate. The organic phase was dried over anhydrous $Na_2SO_4$ and the solvent was evaporated under reduced pressure.

The reduced compound was purified by chromatography on silica gel column. Crude compound/silica gel ratio 1:40. Eluent: ethanol/triethylamine 50:50. A viscous, hardly crystallizable compound was obtained, which was treated with $HNO_3$ in ethyl acetate: a white solid precipitated, corresponding to the compound salt.

M.p. of the nitrate: 206–208° C.
NMR in agreement.

EXAMPLE 4

1-[2-(2,4-Dichlorophenyl)-2-(4-o.methoxyphenyl-piperazine)vinyl]-1H-imidazole

A mixture of 3.3 g (0.013 moles) of 1-(2',4'-dichloro-benzoylmethyl)-imidazole and N-(o-methoxyphenyl)-piperazine 5 g (0.026 moles) in 40 ml of anhydrous butanol and 90 ml of anhydrous toluene, containing p-toluenesulphonic acid as a catalyst, was refluxed for 96 hours. The reaction was checked by NMR. The solvent was evaporated off under reduced pressure, adding several times cyclohexane, to completely remove butanol. The crude compound was taken up in chloroform and quickly washed with ice-water. This organic phase was dried on anhydrous $Na_2SO_4$, and chloroform was evaported under reduced pressure.

The obtained crude compound was in form of an oil.
Yield: about 90%.
NMR in agreement.

EXAMPLE 5

1-[2-(2,4-Dichlorophenyl)-2-(4-o.methoxyphenyl-piperazine)-ethyl]-1H-imidazole

Analogously to Example 3, 5.5 g (0.013 moles) of the vinyl derivative of Example 4 were reacted with 0.57 g (0.0091 moles) of sodium cyanoborohydride in 20 ml of anhydrous methanol.

The reduction product was purified by chromatography on silica gel column. Crude compound/silica gel 1:40. Eluent: ethyl acetate/ethanol 50:50. A viscous, hardly crystallizable compound, was obtained, which was directly treated with HCl in ethanol. A solid compound precipitated, corresponding to the compound salt.

NMR in agreement.

EXAMPLE 6

1-[2-(2,4-Dichlorophenyl)-2-(4-(2-pyridyl)piperazine)-vinyl]-1H-imidazole

A mixture of 3.7 g (0.0145 moles) of 1-(2',4'-dichlorobenzoylmethyl)-imidazole, 5 g (0.029 moles, p=95%) of N-pyridyl-piperazine in 40 ml of anhydrous butanol and 80 ml of anhydrous toluene, added with p-toluenesulphonic acid as a catalyst, was heated to reflux for 24 hours. The reaction was checked by NMR. The solvent was evaporated under reduced pressure, adding cyclohexane several times to completely remove butanol. The crude product was taken up in dichloromethane and quickly washed with ice-water. The organic phase was dried on anhydrous $Na_2SO_4$ and dichloromethane was evaporated off under reduced pressure. The obtained crude compound was in form of an oil, yielding about 90%.

NMR in agreement.

EXAMPLE 7

1-[2-(2,4-Dichlorophenyl)-2-(4-(2-pyridyl)piperazine-ethyl]-1H-imidazole

Analogously to Example 3, 6.6 g (0.0165 moles) of the compound of Example 6 were reacted with 0.63 (0.0115 moles) of sodium cyanoborohydride in 20 ml of anhydrous methanol. The reduction product was purified by chromatography on silica gel column. Crude compound/silica gel ratio 1:40. Eluent: ethyl acetate/triethylamine 50:50. A viscous compound was obtained which solidified upon treatment with ethyl acetate.

The nitrate in ethyl acetate was prepared: the salt was a white solid.

NMR in agreement.

M.p.: 84°–86° C.

EXAMPLES 8–13

Analogously to the above Examples, starting from the corresponding N-phenyl-substituted piperazines, the compounds reported in the following Table were obtained.

TABLE

| Ex. No. | Compound | M.p. (°C.) | R.f. AcOET/TEA 50:50 | C theor. | C found | H theor. | H found | N theor. | N found | RMN (DMSO-d 6) |
|---|---|---|---|---|---|---|---|---|---|---|
| 8 | 1-[2-(2,4-dichlorophenyl)-2-(4-m.trifluoromethyl-phenyl-piperazine)ethyl]-1H-imidazole dinitrate | 91–93 | 0.22 | 44.39 | 44.14 | 3.86 | 4.01 | 14.11 | 13.88 | in agreement |
| 9 | 1-[2-(2,4-dichlorophenyl)-2-(4-o.chlorophenyl-piperazine)ethyl]-1H-imidazole maleate | 115–117 | 0.29 | 54.43 | 54.33 | 4.53 | 4.59 | 10.15 | 9.98 | " |
| 10 | 1-[2-(2,4-dichlorophenyl)-2-(4-o.tolyl-piperazine)ethyl]-1H-imidazole fumarate | 161–163 | 0.35 | 58.75 | 58.64 | 5.27 | 5.36 | 10.54 | 10.37 | " |
| 11 | 1-[2-(2,4-dichlorophenyl)-2-(4-p.chlorophenyl-piperazine)ethyl]-1H-imidazole fumarate | 170–172 | 0.20 | 54.43 | 54.26 | 4.53 | 4.53 | 10.15 | 9.96 | " |
| 12 | 1-[2-(2,4-dichlorophenyl)-2-(4-p.fluorophenyl-piperazine)ethyl]-1H-imidazole fumarate | 163–165 | 0.36 | 56.10 | 55.88 | 4.67 | 4.62 | 10.46 | 10.44 | " |
| 13 | 1-[2-(2,4-dichlorophenyl)-2-(4-m.chlorophenyl-piperazine)ethyl]-1H-imicazole fumarate | 180–182 | 0.32 | 54.43 | 54.19 | 4.53 | 4.61 | 10.15 | 9.85 | " |

For the compounds of Example 8–13, the antibacterial activity against Gram-positive and Gram-negative bacterial strains and the antimycotic activity against blastomycetes and hyphomycetes, in comparison with Miconazole, were evaluated.

EVALUATION OF THE MINIMAL INHIBITORY CONCENTRATIONS (M.I.C.)

| STRAIN | | | Ex. 8 | Ex. 9 | Ex. 10 | Ex. 12 | Ex. 13 | MICONAZOLE (comparison) |
|---|---|---|---|---|---|---|---|---|
| Gram + bacteria | | | | | | | | |
| Staph. aureus | ATCC | 6538P | >100 | 100 | >100 | 100 | 10 | 100 |
| Staph. epidermidis | BB | 0223 | >100 | >100 | >100 | 100 | 10 | 100 |
| Str. faecalis | ATCC | 8043 | 100 | >100 | >100 | 100 | 10 | 100 |
| Str. pyogenes | ATCC | 12380 | 100 | 100 | 10 | 10 | 10 | 10 |
| B. subtilis | ATCC | 6633 | 10 | 100 | 10 | 100 | 10 | 10 |
| B. cereus mucoides | ISM | 65/42 | 10 | 10 | 10 | 100 | 10 | 10 |
| Sarcina lutea | ATCC | 9431 | >100 | >100 | >100 | 10 | 1 | >100 |
| B. antracis | ISM | 68/35 | 10 | 10 | 10 | 100 | 10 | 10 |
| Gram − bacteria | | | | | | | | |
| Esch. coli | K | 12 | >100 | >100 | >100 | >100 | >100 | >100 |
| P. mirabilis | ATCC | 10005 | >100 | >100 | >100 | >100 | >100 | >100 |
| Serratia marcescens | ISM | 67/14 | >100 | >100 | >100 | 100 | 100 | >100 |
| Salm. typhimurium | ATCC | 15277 | >100 | >100 | >100 | >100 | >100 | >100 |

EVALUATION OF THE MINIMAL INHIBITORY CONCENTRATIONS (M.I.C.)

| STRAIN | | | Ex. 8 | Ex. 9 | Ex. 10 | Ex. 12 | Ex. 13 | MICONAZOLE (comparison) |
|---|---|---|---|---|---|---|---|---|
| Salm. cholerae suis | ATCC | 10708 | >100 | >100 | >100 | >100 | >100 | >100 |
| Kleb. pneumoniae | ATCC | 10031 | >100 | >100 | >100 | >100 | >100 | >100 |
| P. vulgaris | ATCC | 6897 | 100 | 100 | 10 | >100 | >100 | 100 |
| Ps. aeruginosa | ATCC | 14502 | >100 | >100 | >100 | >100 | >100 | >100 |
| Bordetella bronchiseptica | ATCC | 4617 | >100 | >100 | >100 | >100 | >100 | >100 |
| Blastomycetes | | | | | | | | |
| Candida albicans | ATCC | 10231 | 100 | 100 | 100 | 1 | 1 | 10 |
| Candida utilis | BB | 0173 | 10 | 10 | 1 | 1 | 1 | 1 |
| Rhodotorula rubra | ISM | 7198 | 10 | 10 | 10 | 1 | 1 | 10 |
| Cryptococcus neoformans | ISM | 7182 | 10 | 10 | 10 | 1 | 1 | 10 |
| Saccharomyces cerevisiae | BB | 0193 | 10 | 10 | 1 | 1 | 1 | 10 |
| Hyphomycetes | | | | | | | | |
| Aspergillus niger | ATCC | 9642 | <0.1 | <0.1 | <0.1 | <0.1 | <0.1 | <0.1 |
| Penicillium funicolosum | ATCC | 9644 | <0.1 | <0.1 | <0.1 | <0.1 | <0.1 | <0.1 |

We claim:

1. A compound of formula I

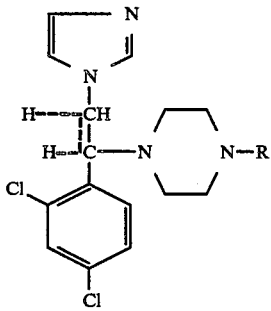

wherein R is phenyl; phenyl mono- or di-substituted by halogen atoms, methyl, methoxy, nitro, or trifluoromethyl groups; or a 2-, 3- or 4-pyridyl group; and pharmaceutically acceptable acid addition salts thereof.

2. A compound according to claim 1 selected from the group consisting of: 1-[2-(2,4-dichlorophenyl)-2-(4-phenyl-piperazine)ethyl]-[b 1H-imidazole; 1-[2-(2,4-dichlorophenyl)-[b 2-(4-o.methoxyphenylpiperazine)ethyl]-1H-imidazole; 1-[2-(2,4-dichlorophenyl)-2-(4-(2-pyridyl)-piperazine)ethyl]-1H-imidazole; 1-[2-(2,4-dichlorophenyl)-[2-(4-o.methoxyphenylpiperazine)e-piperazine)ethyl]-1H-imidazole dinitrate; 1-[2-(2,4-dichlorophenyl)-2-(4-o.chlorophenyl-piperazine)-ethyl]-1H-imidazole maleate; 1-[2-(2,4-dichlorophenyl)-2-(4-o.tolyl-piperazine)ethyl]-1H-imidazole fumarate; 1-[2-(2,4-dichlorophenyl)-2-(4-p.chlorophenyl-piperazine)ethyl]-1H-imidazole fumarate; 1-[2-(2,4-dichlorophenyl)-2-(4-p.fluorophenyl-piperazine)ethyl]-1H-imidazole fumarate; and 1-[2-(2,4-dichlorophenyl)-2-(4-m.chlorophenyl-piperazine)-ethyl]-1H-imidazole fumarate.

3. A pharmaceutical composition having antimycotic and antibacterial activities, containing as the active ingredient a therapeutically effective amount of at least one compound of formula I

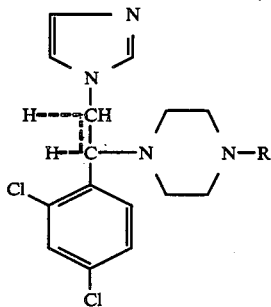

wherein R is phenyl; phenyl mono- or di- substituted by halogen atoms, methyl, methoxy, nitro, or trifluoromethyl; or a 2-, 3- or 4-pyridyl; and pharmaceutically acceptable acid addition salts thereof; together with at least one pharmaceutically acceptable excipient.

* * * * *